US009639917B2

(12) United States Patent
Yu et al.

(10) Patent No.: US 9,639,917 B2
(45) Date of Patent: May 2, 2017

(54) OCT IMAGE MODIFICATION

(71) Applicant: NOVARTIS AG, Basel (CH)

(72) Inventors: Lingfeng Yu, Rancho Santa Margarita, CA (US); Hugang Ren, Cypress, CA (US); Michael Papac, North Tustin, CA (US)

(73) Assignee: Novartis AG, Basel (CH)

( * ) Notice: Subject to any disclaimer, the term of this patent is extended or adjusted under 35 U.S.C. 154(b) by 17 days.

(21) Appl. No.: 14/877,638

(22) Filed: Oct. 7, 2015

(65) Prior Publication Data
US 2016/0343112 A1  Nov. 24, 2016

Related U.S. Application Data

(60) Provisional application No. 62/163,831, filed on May 19, 2015.

(51) Int. Cl.
*G06K 9/00* (2006.01)
*G06T 5/00* (2006.01)
(Continued)

(52) U.S. Cl.
CPC ............. *G06T 5/001* (2013.01); *A61B 3/102* (2013.01); *A61B 3/13* (2013.01); *G06T 5/005* (2013.01); *G06T 7/70* (2017.01); *A61B 90/20* (2016.02); *G02B 21/0012* (2013.01); *G06T 2207/10101* (2013.01); *G06T 2207/30164* (2013.01)

(58) Field of Classification Search
CPC . G06T 2207/10101; G06T 2207/30164; G06T 5/001; G06T 7/004; G06T 5/005
See application file for complete search history.

(56) References Cited

U.S. PATENT DOCUMENTS 6,293,674 B1* 9/2001 Huang ................... A61B 3/102
                                                              351/221
2012/0184846 A1* 7/2012 Izatt ................... G02B 21/0012
                                                              600/425

(Continued)

OTHER PUBLICATIONS

Ehlers, J. et al., "Integrative Advances for OCT-Guided Ophthalmic Surgery and Intraoperative OCT: Microscope Integration, Surgical Instrumentation and Heads-Up Display Surgeon Feedback," www.plosone.org; Aug. 20, 2014, vol. 9, Issue 8, e105224, XP55253425, pp. 1-10.

(Continued)

Primary Examiner — Tom Y Lu
(74) Attorney, Agent, or Firm — Darien Reddick

(57) ABSTRACT

According to some examples, a method for Optical Coherence Tomography (OCT) image modification includes receiving an OCT image of a region of interest of patient tissue from an OCT imaging system configured to direct an OCT beam at the region of interest and determining that an OCT transparent instrument is within the OCT image. The method further includes detecting an artifact in the OCT image, the artifact resulting from the OCT transparent instrument being within a path of the OCT beam. In response to detecting the artifact, the method further includes creating an image modification plan to remove the artifact from the OCT image. The method further includes executing the image modification plan to remove the artifact from the OCT image.

20 Claims, 5 Drawing Sheets

(51) Int. Cl.
*G06T 7/70* (2017.01)
*A61B 3/10* (2006.01)
*A61B 3/13* (2006.01)
*G02B 21/00* (2006.01)
*A61B 90/20* (2016.01)

(56) References Cited

U.S. PATENT DOCUMENTS

2015/0077705 A1* 3/2015 Artsyukhovich .... A61B 3/0025
351/206
2015/0294147 A1* 10/2015 Wisweh ................ A61B 3/102
348/78
2015/0359669 A1 12/2015 Grueebler et al.

OTHER PUBLICATIONS

Girard, M. et al., "Shadow Removal and Contrast Enhancement in Optical Coherence Tomography Images of the Human Optic Nerve Head," Investigative Ophthalmology & Visual Science, Sep. 2011, vol. 52, No. 10, pp. 7738-7748, XP55114474.
Trifonov, B. et al., "Tomographic Reconstruction of Transparent Objects," Eurographics Sympsion on Rendering, 2006, pp. 1-11.
Trifonov, B. et al., "Tomographic Reconstruction of Transparent Objects," Dec. 2006, pp. 1-37.

* cited by examiner

OCT IMAGE MODIFICATION

CROSS REFERENCE TO RELATED APPLICATIONS

This application claims the benefit of U.S. Provisional Application No. 62/163,831, filed May 19, 2015, the contents of both being incorporated herein by reference.

TECHNICAL FIELD

The present disclosure is directed to methods and systems for ophthalmic medical procedures, and more particularly, to methods and systems involving Optical Coherence Tomography (OCT) imaging for such procedures.

BACKGROUND

Many microsurgical procedures require precision cutting and/or removal of various body tissues. For example, Internal Limiting Membrane (ILM) removal and epi-retinal membrane (ERM) removal are useful surgical treatments of different macular surface diseases. However, the surgical techniques for ILM and ERM peeling require skill and patience. Precise and carefully constructed surgical instruments are used for each segment of the surgical technique.

ILM and ERM procedures use a two-step technique. The first step includes gaining an edge of the membrane and the second step includes grasping and peeling the membrane. Some operators use a scraper to gain the edge of the membrane. The operator gently scrapes the membrane to separate membrane edges so that an edge is ready to be grasped. Next, the operator introduces a special forceps to grasp and peel the membrane. However, since each step requires patience and precision, an operator may sometimes scrape and then attempt to grasp the tissue multiple times during a single surgical procedure.

To aid the operator with these types and other types of surgical procedures, operators may use an imaging system that presents a microscope view of the tissue to be treated, such as tissue of the patient's eye. Accordingly, the user of such an imaging system may be provided with a close-up view of the surgical instruments, such as forceps or other tools, as well as the region of the eye that is of interest. In some cases, the operator may also be provided with an Optical Coherence Tomography (OCT) image of the region of the eye that is of interest. OCT imaging generally utilizes near-infrared light and is able to obtain or generate images of tissue beneath the surface. However, the instruments in the eye can generate shadows that inhibit the ability of the OCT system to provide a desired level of clarity. There is a need for continued improvement in the use and operability of surgical systems and tools for various ophthalmic procedures.

SUMMARY

According to some examples, methods for OCT image modification may include receiving an OCT image of a region of interest of patient tissue from an OCT imaging system configured to direct an OCT beam at the region of interest and determining that an OCT transparent instrument is within the OCT image. The method may include detecting an artifact in the OCT image. The artifact may result from the OCT transparent instrument being within a path of the OCT beam. In response to detecting the artifact, the method may include creating an image modification plan to remove the artifact from the OCT image. The method may include executing the image modification plan to remove the artifact from the OCT image.

According to some examples, methods for OCT image modification of an ophthalmic region of interest may include receiving an OCT image of a region of interest of ophthalmic tissue from an OCT imaging system. The method may include determining that an OCT transparent instrument is within the OCT image. In response to determining that an OCT transparent instrument is within the image, the method may include determining a set of parameters associated with the OCT transparent instrument. The parameters may include characteristics of the OCT transparent instrument and placement of the OCT transparent instrument. The method may include, based on the set of parameters, modifying the OCT image to remove an artifact within the OCT image. The artifact may be a result of the OCT transparent instrument being within a path of an OCT beam used by the OCT imaging system.

According to some examples, ophthalmic imaging systems may include an OCT imaging system arranged to capture real-time images of a region of interest and may include a display system to present images captured by the OCT imaging system to a user. The ophthalmic imaging system may include a control system comprising a processor and a memory. The memory may include machine readable instructions that when executed by the processor, cause the control system to receive an image of a region of interest from the OCT imaging system, determine that an OCT transparent instrument is within the image, and in response to determining that an OCT transparent instrument is within the image, obtaining a set of parameters associated with the OCT transparent instrument. The machine readable instructions may cause the system to create an image modification plan based on the set of parameters. The image modification plan may be arranged to remove an artifact within the image. The machine readable instructions may cause the system to execute the image modification plan to create a modified image and display the modified image through the display system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
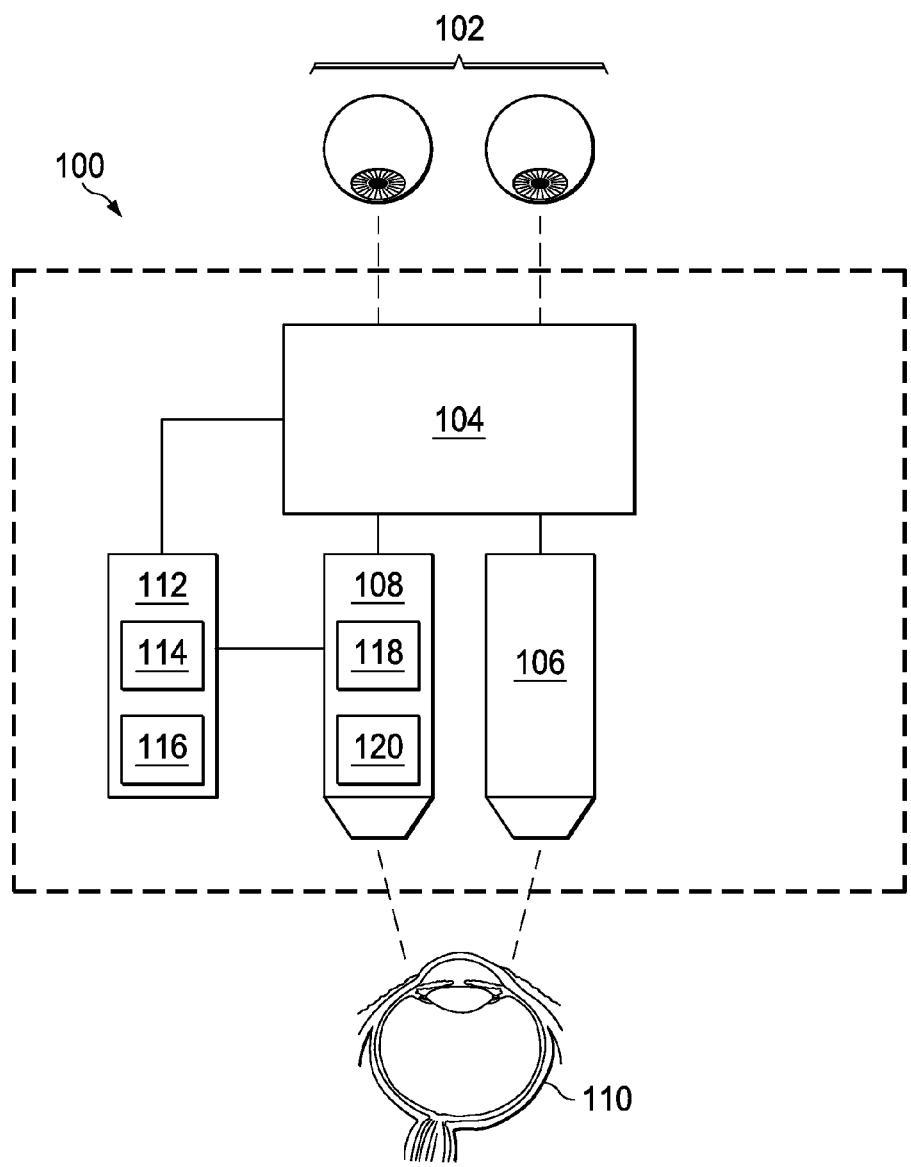
FIG. 1 is a diagram showing an illustrative ophthalmic surgical system.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure is directed to methods and systems for modifying or correcting for clarity an OCT image that has been affected by use or presence of an OCT transparent surgical instrument. In various procedures, a user may observe a region of interest, such as an eye of a patient, using both an imaging system that includes a microscope imaging system and an OCT imaging system. Such an imaging system permits a user to observe both a conventional microscope image and an OCT image while using a surgical instrument to perform an ophthalmic surgical procedure such as an ILM removal. The conventional microscope image is observed using light that is within the visible spectrum having a wavelength ranging between about 400 nanometers and 700 nanometers. The OCT image is usually generated using light in the near infrared range having a wavelength within a range of about 700 nanometers to 1700 nanometers. It is, however, also possible to obtain OCT images using light in the visible spectrum range. Thus, an OCT image may be obtained using light within any practicable wavelength range. In some cases, the OCT image may provide a cross-sectional view of the region of interest within the eye and may be used to visualize tissue below the outer surface tissue. A conventional surgical tool will block the light within the OCT spectrum that is used by the OCT imaging system, thus blocking the entire view of the region of interest below the surface of the tissue. In contrast, an OCT transparent instrument can still be seen within the microscope image and yet will not block all the light used to generate the OCT image.

OCT transparent instruments may be placed in the OCT beam path between the tissue being imaged and the OCT capture device that measures the OCT light to capture an image. The OCT transparent nature of such instruments allows the OCT light to pass and thus the tissue underneath the OCT instrument can still be captured. But, an OCT transparent instrument may still have a small effect on the OCT beam. Thus, the OCT transparent instrument may sometimes cause artifacts to be present within the OCT image. For example, an artifact may be a break in the image of the tissue beneath the current location of the OCT transparent instrument. Such a break is a result of a longer optical path length between the OCT capture device and the tissue beneath the OCT transparent instrument. There is a different optical path length because the index of refraction of the OCT transparent instrument is different than the index of refraction of the surrounding fluids. Due to the different index of refraction of the OCT transparent instrument, OCT light passing through the OCT transparent instrument travels a longer distance than light not passing through the OCT transparent instrument.

According to principles described herein, the present disclosure is directed to modifying an OCT image to correct any artifacts caused by the presence of the OCT transparent instrument. In some examples, this may be done by analyzing the OCT image to detect characteristics of the artifact and making adjustments to the OCT image to remove the artifact. In other examples, parameters of the OCT transparent instrument, such as position, orientation, shape, and index of refraction may be obtained. Using such parameters, an image modification plan may be created. The image modification plan may be designed to use the known parameters to "reverse" the effects that the OCT transparent instrument has on the OCT image. The image modification plan may then be executed and the modified image may be presented to a user. As the OCT transparent instrument changes position and orientation in real-time, the image modification process is applied to newly captured images to provide a user with a real-time, modified view of the OCT image.

FIG. 1 is a diagram showing an illustrative ophthalmic imaging system 100. According to the present example, the ophthalmic imaging system 100 includes an image viewer 104, a microscope imaging system 106, an OCT imaging system 108, and a control system 112. The ophthalmic imaging system 100 provides a user 102 with a microscope view and an OCT image of the region of interest within a target region of the patient's body. In this example, the target region is an eye 110 of the patient.

The microscope imaging system 106 obtains images of the patient's eye 110 using light within the visible spectrum. The visible spectrum defines the wavelength range of light that is visible to the human eye. The visible spectrum includes electromagnetic radiation having a wavelength that is, as indicated above, generally within a range of about 400 nanometers to 700 nanometers, though this wavelength range may vary slightly for different individuals. The microscope imaging system 106 may use a system of lenses to provide a close-up view of the patient's eye 110 or even a specific region of interest within the patient's eye 110. Such an image may then be provided to the image viewer 104.

The OCT imaging system 108 obtains OCT images of the patient's eye 110. It uses various techniques to obtain depth resolved images of the patient's tissue beneath the surface of the tissue that are not able to be obtained from the use of a standard microscope. This is done using coherence gating based on light that is within the OCT spectrum. As indicated above, this range includes electromagnetic radiation having a wavelength between about 700 nanometers and 2600 nanometers, and in some cases can be extended to the visible light range of about 400 nanometers to 700 nanometers. By using coherence gating, the OCT imaging system 108 can display an image of tissue below the surface tissue and generate a cross-sectional view of such tissue. As such, the OCT imaging system 108 may be used to obtain a cross-sectional view of the region of interest at which the user 102 is operating. A benefit of this is that the user 102 is able to see how interactions between the surgical instrument and the surface of an ILM affect the tissue below the surface of the ILM. Specifically, the user 102 can use the cross-sectional image to help avoid accidental damage to the underlying retina. In some examples, the OCT imaging system 108 is integrated with the conventional microscope imaging system 106. In some examples, however, the OCT imaging system 108 may be a separate apparatus that provides the OCT images to the image viewer 104.

The OCT imaging system 108 includes various components that are used to perform the OCT imaging function. For example, the OCT imaging system 108 may include an OCT light source 118 to project an OCT beam at a region of interest. The OCT imaging system 108 may also include an OCT capture device 120 that detects OCT light reflected from the region of interest. The OCT imaging system 108 then uses the information obtained by the OCT capture device 120 to construct an image of the region of interest. In some examples, the image may be a two-dimensional cross-section of the region of interest that provides a view beneath the surface of tissue within the region of interest. In some examples, the image may be a three-dimensional image that also provides a three-dimensional view beneath the surface.

The image viewer 104 displays to a user 102 or other operator, the images obtained by both the microscope imaging system 106 and the OCT imaging system 108. The image viewer 104 may display the images in a variety of ways, such as on a monitor, display screen, on the microscope eyepiece, or in other ways. In some examples, the microscope imaging system 106 may provide stereoscopic images formed of at least two images. The image viewer 104 may display the at least two images to different eyes of the user 102, thus creating a three dimensional effect.

The control system 112 is a computing system that may process images obtained from the OCT imaging system 108. These images, which may contain artifacts, may be modified by the control system 112 to remove the artifacts. The modified images may then be provided to the image viewer 104. In some examples, the control system 112 may be integrated with the OCT imaging system 108. In some examples, the control system 112 may be integrated with the image viewer 104. In some examples, the control system 112 is a discrete component that is separate from, and in communication with, the image viewer 104 and the OCT imaging system 108.

The control system 112 also includes a processor 114 and a memory 116. The memory 116 may include various types of memory including volatile memory (such as Random Access Memory (RAM)) and non-volatile memory (such as solid state storage). The memory 116 may store computer readable instructions, that when executed by the processor 114, cause the control system 112 to perform various functions, including the image modification functions described herein. The memory 116 may also store data representing images captured by the OCT imaging system 108 as well as modified versions of those images. The memory 116 may also store parameters associated with an OCT transparent instrument. Such parameters will be described in further detail below.

Figure 2:
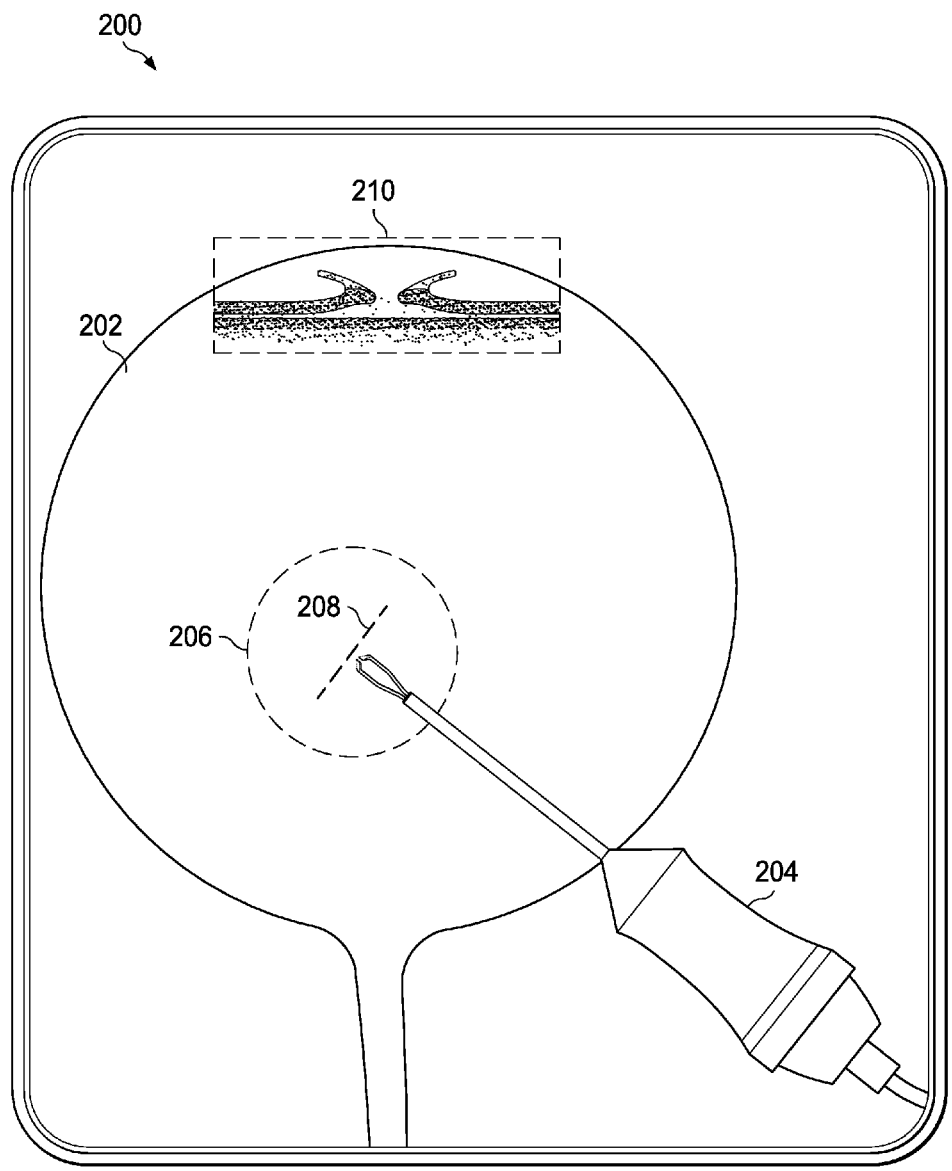
FIG. 2 is a diagram showing an illustrative image of a patient's eye as may be seen through an OCT-enabled microscope during a surgical procedure.

FIG. 2 is a diagram showing an illustrative combined microscope and OCT view 200 of a patient's eye as presented or displayed by the image viewer 104. According to the present example, the image viewer 104 (FIG. 1) overlays an OCT image 210 on a microscope image 202. Thus, the user can view a potential region of interest 206 along with the surgical instrument 204 being used to operate within the region of interest 206. The dotted line 208 in FIG. 2 represents the cross-sectional line at which the cross-sectional OCT image 210 is taken. Thus, as may be seen, image viewer (e.g., 104, FIG. 1) projects the OCT image 210 onto the microscope image 202 in a manner permitting the user to visually observe both images 202, 210 at once.

Figures 3A, 3B:
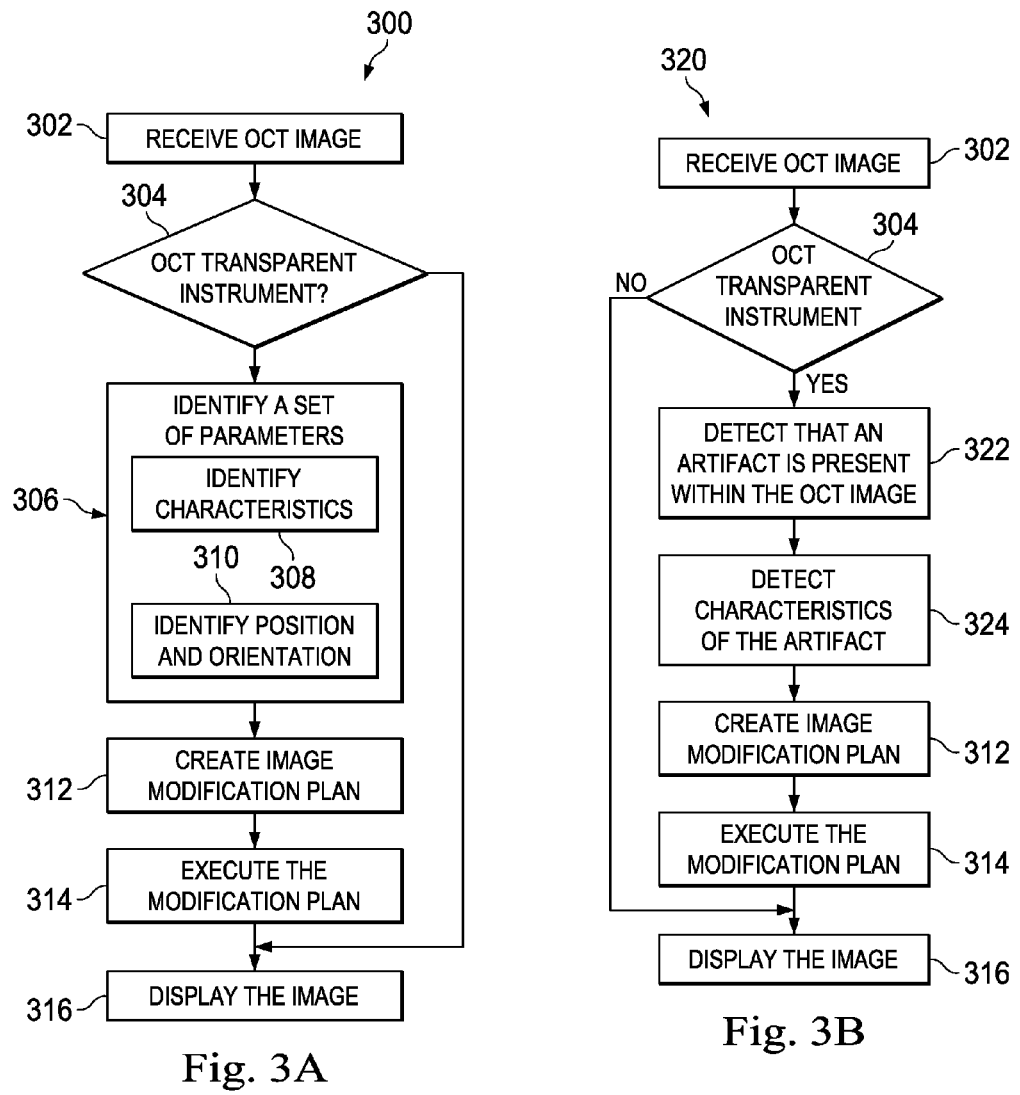
FIGS. 3A and 3B are flowcharts showing illustrative methods for OCT image modification.

FIG. 3A is a flowchart showing an illustrative method 300 for OCT image modification based on parameters of an OCT transparent tool. In some examples, the method 300 is performed by a control system (e.g., 112, FIG. 1). According to the present example, the method 300 includes a step 302 for receiving an OCT image from an OCT imaging system (e.g., 108, FIG. 1). The OCT image may be a two-dimensional image or a three-dimensional image.

The method 300 further includes a step 304 for determining whether an OCT transparent instrument is present within the image. This may be done in a variety of manners. In some examples, the control system analyzes the image itself to determine whether an OCT transparent instrument is present. In such a case, the control system determines that an OCT transparent instrument is present within the OCT image by performing the steps associated with such an analysis. This analysis may be done by analyzing the area of the image above the region of interest where an OCT transparent instrument is likely to be. An OCT transparent instrument is not completely transparent and thus may still appear in some form recognizable by a function designed to analyze the OCT image, such as by identifying artifacts or wavelength or image discrepancies that manifest themselves in the image data.

In some cases, an OCT transparent instrument may be made of a material that is semi-transparent to OCT light. This allows the user to better visualize the instrument within the OCT image as well as allow for the OCT light to pass through the instrument and provide an image of the tissue underneath the instrument. In some examples, other mechanisms may be used to help view the OCT transparent instrument within the OCT image. For example, a high frequency ultrasound imaging system may be used in conjunction with the OCT imaging system to produce an image of both the OCT transparent instrument and the underlying tissue together.

In some examples, a user may indicate to the control system that an OCT transparent instrument is being used. In such a case, the control system determines that an OCT transparent instrument is present within the OCT image by receiving such an indication from the user. Such an indication may be made through a user interface associated with the control system and may include an input or other setting. Other methods for determining that an OCT transparent instrument is present are also contemplated. For example, the control system may determine that an OCT transparent instrument is present within the OCT image by receiving data from sensors or detectors, such as fundus imagers, that detect the presence of such an instrument near the region of interest being observed by the OCT imaging system.

If it is determined that there is no OCT transparent instrument within the OCT image, then the control system may perform no further processing of the image. In such a situation, the method 300 proceeds to step 316 at which the original OCT image is displayed. But, if at step 304 it is determined that there is an OCT transparent instrument within the image, then the method 300 proceeds to step 306.

Step 306 is a step of identifying a set of parameters associated with the OCT transparent instrument. Step 306 includes a step 308 for identifying characteristics of the OCT transparent instrument. Such characteristics may include, for example, the shape of the OCT transparent instrument and the index of refraction of the OCT transparent instrument. Such parameters may be referred to as static parameters because they do not change. Other static parameters are also contemplated.

The static parameters may be identified in a variety of ways. In some examples, the control system may have a database that stores data related to a plurality of different OCT transparent instruments. For each different OCT transparent instrument, there may be an entry within the database that provides the shape of the instrument, its refractive index, and other static parameters. To determine which of the plurality of OCT transparent instruments is present within an OCT image, a function may be applied to the OCT image that recognizes and automatically identifies the instrument. For example, the control system may determine the cross-sectional shape of the OCT transparent instrument and matches it to one of the entries within the database. In some examples, however, a user may simply input the type of OCT transparent instrument being used and based on the input, the control system may look up the characteristics of that OCT transparent instrument in the database to determine the appropriate static parameters, such as, for example, the shape and index of refraction for that OCT transparent instrument.

Step 306 further includes a step 310 for identifying a position and an orientation of the OCT transparent instrument. Such parameters will change in real-time as the user manipulates the OCT transparent instrument to perform surgical related operations. Thus, such parameters may be referred to as dynamic parameters. The dynamic parameters are important because the position and orientation of the OCT transparent instrument can affect the artifact within the OCT image. While the dynamic parameters of position and orientation are identified, other dynamic parameters also may be used.

The dynamic parameters, such as position and orientation, of the OCT transparent instrument may be determined in a variety of manners. In some examples, the OCT transparent instrument may have position or orientation sensing devices attached thereto or embedded within that can detect such information. For example, the OCT transparent instrument may have a gyroscope associated therewith to determine the current orientation. In some other examples, however, the dynamic parameters such as position and orientation may be determined by analysis of the OCT image itself. Specifically, a function may be applied that detects the boundaries of the OCT transparent instrument within the image. The function can also determine the boundaries of the tissue within the region of interest. Thus, the position of the OCT transparent instrument with respect to the tissue may be determined. Other arrangements use a combination of detector inputs and analysis for detection. Still other arrangements and systems are also contemplated.

The method 300 further includes a step for creating an image modification plan 312. The image modification plan is based on the obtained parameters, both static and dynamic. Using such parameters, the control system may determine how the image of the underlying tissue will be affected to create the artifact. These effects can then be "reversed" in order to remove the artifact. In some examples, the image modification plan may be designed to account for the difference in optical path length at positions of the tissue that are underneath the OCT transparent instrument. Thus, the image modification plan may relate to translations of portions of the tissue within the OCT image to remove the artifact. In some examples, the image modification plan may adjust the intensity of the OCT image that was affected by the presence of the OCT transparent instrument. In some examples, the image modification plan may perform a phase adjustment to help remove the artifact. In other words, the image modification plan accounts for the phase difference in the OCT beam resulting from passing through the OCT transparent instrument. The image modification plan may also account for differences in OCT signal strength resulting from the OCT beam passing through the OCT transparent instrument. Thus, creation of the image modification plan may involve determining a difference in optical path length, a difference in OCT signal strength, and/or a difference in OCT signal phase resulting from the OCT signal passing through the OCT transparent instrument. Such differences may then be used to determine how to remove the artifacts created by the OCT transparent image.

At a step 314, the control system executes the image modification plan. In other words, the control system modifies the OCT image to substantially remove the artifact. In some examples, a new digital OCT image is created and stored within the memory of the control system.

At step 316, the OCT image is displayed to a user. The image displayed is either the original image in the case that no OCT transparent instrument is present, or the modified image in the case that an OCT transparent instrument is present. In some examples, the control system may be configured to display images in a manner that provides the user with a modified view of the region of interest. For example, the user may be provided with a video stream comprising a series of OCT images that have been modified to substantially remove the artifacts resulting from the OCT transparent instrument. This may be done in real time such that the image appears as live video to a user. Alternatively, this may be done in what appears as still images. Each image may be modified with its own image modification plan as the position and orientation of the OCT transparent instrument moves within the surgical space.

FIG. 3B is a flowchart showing an illustrative method 320 for OCT image modification based on characteristics of an artifact. In some examples, an image modification plan may be formed without analysis of the parameters associated with the OCT transparent instrument. For example, after determining that an OCT transparent instrument is present, the method 320 includes a step 322 for detecting that an artifact is present within the OCT image. The control system may also determine, by the nature of the artifact, that such an artifact is a result of an OCT transparent instrument being present.

The method 320 further includes a step 324 for detecting various characteristics of the artifact. Such characteristics may be useful for determining how to remove the artifact. Such characteristics may include, for example, boundaries of a break. Such characteristics may also include differences in intensity or phase of the OCT image. The characteristics of the artifact can be used to determine an image modification plan as described above with reference to step 312. For example, the image modification plan may define how portions of the OCT image that are within the boundaries are to be translated. The translation of such portions of the OCT image with respect to portions of the OCT image outside the boundaries of the artifact causes the OCT image to appear as if there were no artifacts resulting from the presence of the OCT transparent instrument. In other words, the translation substantially removes the artifacts. In some examples, both parameters of the OCT transparent image and characteristics of the break may be determined and used to create an image modification plan.

Figure 4A:
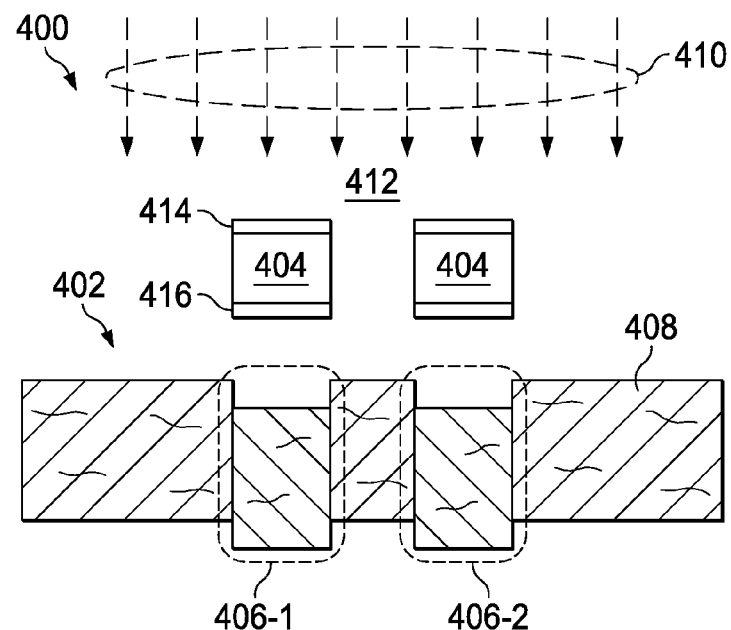
FIGS. 4A and 4B respectively show stylized illustrative OCT images before and after an image modification process.
Figure 4B:
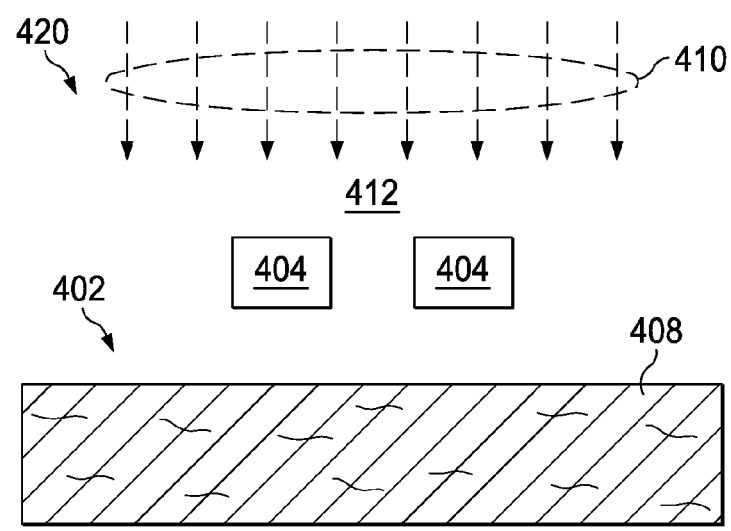

FIGS. 4A and 4B show illustrative OCT images 400, 420 before and after an image modification process, respectively. Present within the OCT image 400 of FIG. 4A is tissue 408 within the region of interest 402, a cross-section of an OCT transparent instrument 404, and artifacts 406-1, 406-2 resulting from the presence of the OCT transparent instrument 404. An OCT beam 410, while not actually visible within the actual OCT image 400, is illustrated for purposes of understanding.

In the present example, the OCT transparent instrument 404 may be a forceps. Thus, the cross-sectional view of the OCT transparent instrument 404 within the OCT image 400 has two sections, each section corresponding to one arm of the forceps. As described above, while the OCT transparent instrument 404 allows the OCT beam 410 to pass through, it still affects the OCT beam 410 and thus the image captured by the capture device. Specifically, the OCT transparent instrument 404 has a different index of refraction than the surrounding material 412. In the example of a retinal surgery, the surrounding material 412 may be retinal fluid.

Thus, the presence of the OCT transparent instrument 404 creates the artifacts 406-1, 406-2 as illustrated. In the present example, the artifacts 406-1, 406-2 appear as breaks within the surface of the tissue 408. The breaks are results of the difference in optical path length between regions of the tissue 408 that are blocked by the OCT transparent instrument 404 and regions of the tissue 408 that are not blocked by the OCT transparent instrument 404.

As described above, various parameters associated with the OCT transparent instrument 404 are determined. Specifically, by knowing one or more static parameters and one or more dynamic parameters, such as for example, the index of refraction and/or the shape of the OCT transparent instrument 404 as well as its position with respect to the surface of the tissue 408, the control system may determine the effect that the presence of the OCT transparent instrument 404 will have on the tissue 408 beneath it. The OCT image 400 may then be modified to reverse these effects.

In some examples, the position of the OCT transparent instrument 404 is determined using a segmentation function. The segmentation function determines the relevant boundaries of the OCT transparent instrument 404. Specifically, the segmentation function may produce top lines 414 and bottom lines 416 representing the top surface and bottom surface of the OCT transparent instrument 404 respectively. By knowing the positions of such boundaries, static and dynamic parameters may be determined. For example, by knowing the position of such boundaries, the thickness of the OCT transparent instrument 404 as well as the distance between the OCT transparent instrument 404 and the tissue 408 may be determined. Thus, segmentation may provide data used to determine static parameters at step 308 and dynamic parameters at step 310 of FIG. 3A. This information may be used to determine by how much the region of tissue 408 beneath the OCT transparent instrument 404 should be translated or otherwise modified to remove the artifacts 406-1, 406-2.

While FIG. 4A illustrates a case where the OCT transparent instrument 404 is equal in thickness and distance from the tissue 408 across the width of the image, practical situations may not be as straightforward. The user may be holding the OCT transparent instrument 404 at an angle and thus the top and bottom surfaces will not be straight lines parallel with the surface of the tissue 408. In some examples, the function that determines how far to translate the portions of the OCT image 400 corresponding to the underlying tissue 408 involves splitting the image into a set of vertical slices. For each slice, the thickness of the OCT transparent instrument 404 may be determined. Knowing the thickness and the index of refraction of the OCT transparent material, the difference in optical path length can be calculated. Using such information, it may be determined how the tissue portion of the respective slice should be translated to remove the artifacts 406-1, 406-2. The width of each slice may be based on the resolution of the OCT image 400.

FIG. 4B illustrates a modified image 420 that corresponds to the original OCT image 400, except that the artifacts 406-1, 406-2 have been removed by the control system. Specifically, using the methods described above with respect to FIG. 3, the control system modified the OCT image 400 to create the modified OCT image 420.

As described above, in some examples, an image modification plan may be formed without analysis of the parameters associated with the OCT transparent instrument 404. In the present example, the artifacts 406-1, 406-2 appear as breaks within the image. One type of characteristic that may be determined by the control system is the locations of the boundaries of the artifacts 406-1, 406-2.

The characteristics of the artifacts 406-1, 406-2, such as the location of the boundaries, can be used to determine an image modification plan that removes the artifacts 406-1, 406-2. For example, the image modification plan may define how portions of the OCT image 400 that are within the boundaries are to be translated. The translation of such portions of the OCT image 400 with respect to portions of the OCT image 400 outside the boundaries of the artifact causes the OCT image 400 to appear as if there were no artifacts resulting from the presence of the OCT transparent instrument 404. In other words, the translation substantially removes the artifacts 406-1, 406-2.

Figure 5A:
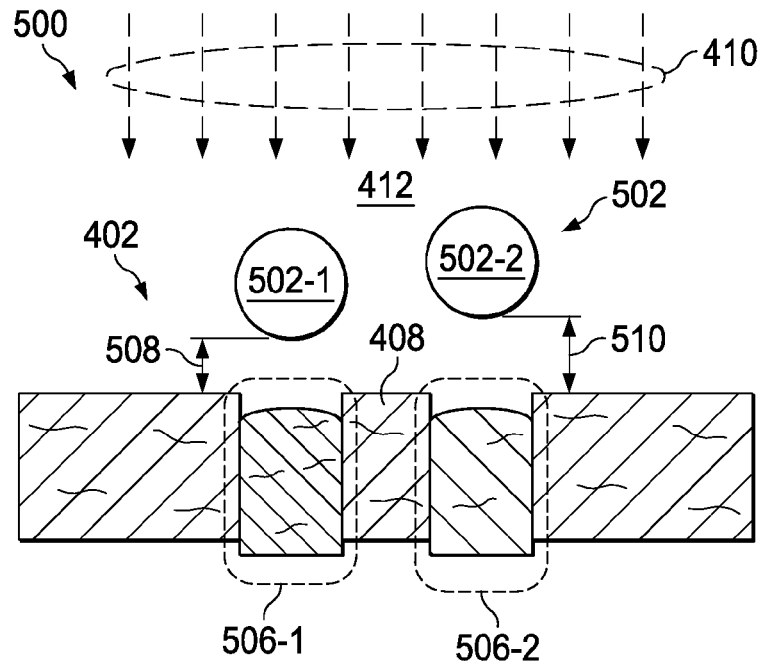
FIGS. 5A and 5B respectively show stylized illustrative OCT images before and after an image modification process.
Figure 5B:
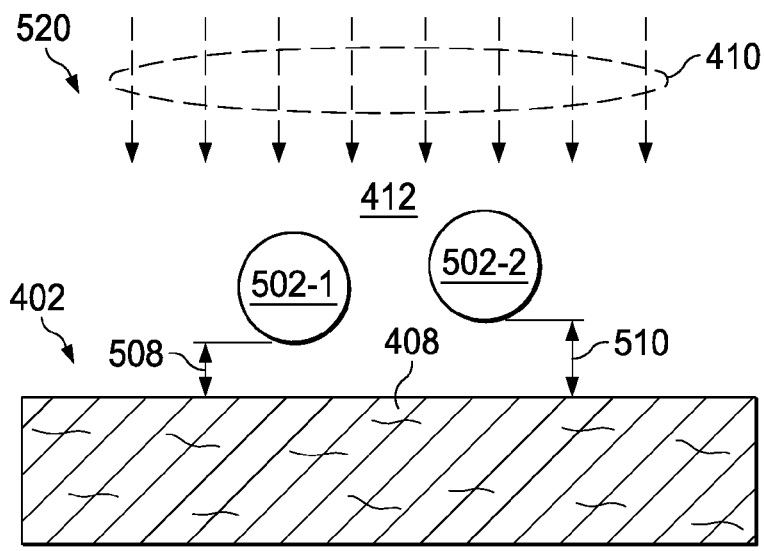

FIGS. 5A and 5B show additional illustrative OCT images 500, 520 before and after an image modification process. In some examples, the OCT transparent instrument 502 may have a curved shape that acts as a lens and thus focuses the OCT beam 410 in undesirable ways and thus creates a more complex artifact. But, by knowing the curvature of the OCT transparent instrument 502, the image modification plan can take such focus effects into account and effectively reverse such effects.

FIG. 5A illustrates an OCT image 500 before being modified. Present within the OCT image 500 is tissue 408 within the region of interest 402, a cross-section of an OCT transparent instrument 502, and artifacts 506-1, 506-2 resulting from the presence of the OCT transparent instrument 502. An OCT beam 410, while not actually visible within the OCT image 500, is again illustrated for purposes of understanding.

In this example, the OCT transparent instrument 502 has rounded edges. Again, the OCT transparent instrument 502 may be a forceps. The cross-sectional view thus shows a first arm 502-1 and a second arm 502-2. The first arm 502-1 is at a first distance 508 from the surface of the tissue 408. The second arm 502-2 is at a second distance 510 from the surface of the tissue 408.

The curved nature of the top and bottom surfaces of the OCT transparent instrument 502 will create a lens effect on the OCT beam 410. In other words, the OCT beam 410 will be redirected at different angles at different points along the surface. But, the nature of such focusing effect may be determined by knowing static parameters such as the curvature of the top and bottom surfaces as well as dynamic parameters such as the distance between the curved surfaces and the underlying tissue 408. Such parameters may be determined as described above with reference to FIGS. 3, 4A, and 4B. Such parameters can thus be used to reverse the effects the cause the artifacts 506-1, 506-2 and thus create a modified image that is substantially artifact-free.

FIG. 5B illustrates a modified image 520 that corresponds to the original image 500, except that the control system has removed artifacts 506-1, 506-2. Specifically, using the methods described above with respect to FIG. 3, the OCT image 500 of FIG. 5A is modified to create the modified OCT image 520 in FIG. 5B.

It is noted that the artifacts 406-1, 406-2, 506-1, 506-2 illustrated in FIGS. 4A and 5A are not necessarily representative of an artifact that would be produced by the illustrated OCT transparent instrument shapes. Rather, the artifacts 406-1, 406-2, 506-1, 506-2 are shown for purposes of clarity and understanding.

In some examples, the image modification plan may include other steps to modify an image to be substantially artifact-free. For example, in addition to spatial changes as were shown and discussed with reference to FIGS. 4A, 4B, 5A, and 5B, the control system can modify the image intensity of the artifacts 406-1, 406-2, 506-1, 506-2 as well. For example, the image intensity of an artifact may be altered as a result of the OCT beam 410 passing through the OCT transparent instrument 404, 502. Thus, in some examples, the control system compensates for the image intensity difference of the artifacts 406-1, 406-2, 506-1, 506-2. In some examples, to accomplish this, the control system may use a function to analyze the image intensity at portions of the tissue 408 that are not underneath the OCT transparent instrument. The control system may then modify portions of the image corresponding to the region of tissue 408 beneath the OCT transparent instrument to have image intensity like the other portions of tissue 408.

While the examples in FIG. 4A, 4B, 5A, and 5B relate to two-dimensional images, some embodiments may perform similar functions on three-dimensional images. Specifically, the parameters of an OCT transparent instrument may be used to determine the effect on underlying tissue 408 in three dimensions. Such effects can then be reversed to provide a modified three-dimensional image that is substantially artifact-free.

Using principles described herein, an OCT image provided to the user of an imaging system can be automatically modified to remove artifacts caused by the presence of the OCT transparent instrument. Such artifacts may cause confusion to the viewer. Thus, by removing such artifacts the user is provided with a better view of the underlying tissue. This improved image translates to more accurate information for the user, and may lead to better patient outcomes.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method for Optical Coherence Tomography (OCT) image modification, the method performed by a computing system, the method comprising:
    receiving an OCT image of a region of interest of patient tissue from an OCT imaging system configured to direct an OCT beam at the region of interest;
    determining that an OCT transparent instrument is within the OCT image;
    detecting an artifact in the OCT image, the artifact resulting from the OCT transparent instrument being within a path of the OCT beam;
    in response to detecting the artifact, creating an image modification plan to remove the artifact from the OCT image; and
    executing the image modification plan to remove the artifact from the OCT image.

2. The method of claim 1, wherein the artifact comprises a break in a portion of the image.

3. The method of claim 2, further comprising:
    detecting boundaries of the break; and
    translating a portion of the image within the boundaries so as to remove the break.

4. The method of claim 1, further comprising determining a set of parameters associated with the OCT transparent instrument, wherein the set of parameters is used by the image modification plan to remove the artifact from the OCT image.

5. The method of claim 4, wherein the set of parameters includes a position of the OCT transparent instrument, an orientation of the OCT transparent instrument, a thickness of the OCT transparent instrument, an index of refraction of the OCT transparent instrument, and a shape of the OCT transparent instrument.

6. The method of claim 5, further comprising, using the parameters, determining a difference in optical path length resulting from the OCT transparent instrument being in a path between the source of the OCT beam and tissue within the region of interest.

7. The method of claim 6, further comprising, translating the image of the region of interest based on the difference in optical path length.

8. The method of claim 1, wherein the image modification plan is arranged to remove the artifact in part by accounting for curves of the OCT transparent instrument that create a lens effect on the OCT beam.

9. The method of claim 1, wherein the image modification plan is arranged to remove the artifact in part by accounting for at least one of: differences in intensity resulting from the OCT beam passing through the OCT transparent instrument and differences in phase resulting from the OCT beam passing through the OCT transparent instrument.

10. The method of claim 1, further comprising utilizing an ultrasound imaging system in conjunction with the OCT imaging system to cause the OCT image to include the OCT transparent instrument.

11. The method of claim 1, wherein determining that the OCT transparent instrument is within the image comprises at least one of: analyzing the image and receiving data from a sensor.

12. A method for Optical Coherence Tomography (OCT) image modification of an ophthalmic region of interest, the method performed by a computing system, the method comprising:
    receiving from an OCT imaging system, an OCT image of a region of interest of ophthalmic tissue;
    determining that an OCT transparent instrument is within the OCT image;
    in response to determining that an OCT transparent instrument is within the OCT image, determining a set of parameters associated with the OCT transparent instrument, the parameters including characteristics of the OCT transparent instrument and placement of the OCT transparent instrument; and
    based on the set of parameters, modifying the OCT image to remove an artifact from the OCT image, the artifact being a result of the OCT transparent instrument being within a path of an OCT beam used by the OCT imaging system.

13. The method of claim 12, wherein the characteristics of the OCT transparent instrument comprise an index of refraction of a material forming the OCT transparent instrument and a shape of the OCT transparent instrument, and wherein placement of the OCT transparent instrument comprises position of the OCT transparent instrument and orientation of the OCT transparent instrument.

14. The method of claim 13, wherein placement of the OCT transparent instrument is determined through at least one of: analysis of the image and receiving data from a sensor.

15. The method of claim 12, further comprising, based on the parameters, determining at least one of:

a difference in optical path length caused by the OCT transparent instrument being in a path between the source of the OCT beam and tissue within the region of interest, a difference in OCT signal strength, and a difference in OCT signal phase.

16. The method of claim 12, further comprising, receiving additional images from the OCT imaging system;

receiving modified sets of parameters for the additional images, the modified sets of parameters being dependent on varying positions and orientations of the OCT transparent instrument;

adjusting the additional images based on the sets of parameters to create additional modified images; and displaying the additional images to a user in a real-time.

17. The method of claim 12, wherein the image is a three dimensional image.

18. An ophthalmic imaging system comprising:

an Optical Coherence Tomography (OCT) imaging system adapted to capture real-time images of a region of interest;

a display system adapted to present images captured by the OCT imaging system to a user;

a control system comprising a processor and a memory, the memory comprising machine readable instructions that when executed by the processor, cause the control system to:

receive an image of a region of interest from the OCT imaging system;

determine that an OCT transparent instrument is within the image;

in response to determining that an OCT transparent instrument is within the image, obtain a set of parameters associated with the OCT transparent instrument;

create an image modification plan based on the obtained set of parameters, the image modification plan being arranged to remove an artifact within the image;

execute the image modification plan to create a modified image; and display the modified image via the display system.

19. The system of claim 18, wherein the machine readable instructions further cause the control system to:

receive additional images from the OCT imaging system;

receive modified sets of parameters for the OCT transparent instrument in the additional images, the modified sets of parameters being based on positions and orientations of the OCT transparent instrument; and modify the additional images based on the sets of parameters to create additional modified images.

20. The system of claim 19, wherein the machine readable instructions further cause the control system to display the additional modified images in real-time.

* * * * *